(12) United States Patent
Boyd

(10) Patent No.: US 7,229,444 B2
(45) Date of Patent: Jun. 12, 2007

(54) TROCHANTERIC CERCLAGE PLATE

(75) Inventor: Harold S. Boyd, Salem, OR (US)

(73) Assignee: Howmedica Osteonics Corp., Mahwah, NJ (US)

( * ) Notice: Subject to any disclaimer, the term of this patent is extended or adjusted under 35 U.S.C. 154(b) by 178 days.

(21) Appl. No.: 10/925,427

(22) Filed: Aug. 25, 2004

(65) Prior Publication Data

US 2006/0058795 A1    Mar. 16, 2006

(51) Int. Cl.
*A61B 17/58* (2006.01)
(52) U.S. Cl. ....................................... 606/69
(58) Field of Classification Search ............ 606/69–71, 606/74
See application file for complete search history.

(56) References Cited

U.S. PATENT DOCUMENTS

| | | | |
|---|---|---|---|
| 3,824,995 A * | 7/1974 | Getscher et al. | 606/69 |
| 4,269,180 A | 5/1981 | Dall et al. | |
| 4,565,193 A * | 1/1986 | Streli | 606/69 |
| 4,651,724 A * | 3/1987 | Berentey et al. | 606/69 |
| 4,988,350 A | 1/1991 | Herzberg | |
| 5,015,248 A | 5/1991 | Burstein et al. | |
| 5,190,545 A | 3/1993 | Corsi et al. | |
| 5,462,547 A | 10/1995 | Weigum | |
| 5,665,089 A | 9/1997 | Dall et al. | |
| 5,810,822 A * | 9/1998 | Mortier | 606/69 |
| 6,066,141 A | 5/2000 | Dall et al. | |
| 6,338,734 B1 | 1/2002 | Burke et al. | |
| 6,503,281 B1 * | 1/2003 | Mallory | 623/22.15 |

* cited by examiner

*Primary Examiner*—Eduardo C. Robert
*Assistant Examiner*—Annette Reimers
(74) *Attorney, Agent, or Firm*—Lerner, David, Littenberg, Krumholz & Mentlink, LLP

(57) ABSTRACT

A bone fixation system has at least one cerclage cable and an elongate bone plate. The bone plate has a bone contacting surface, first and second spaced side portions and an outer surface opposite said bone contacting surface. The elongate plate includes a plurality of apertures or openings therethrough surrounded by the side portions. The apertures extending from the outer surface to the bone contacting surface and being spaced to form bridge portions between adjacent apertures. Each of the bridge portions including at least two pairs of through bores extending between the first and second side portions for receiving cerclage cable. Each of the first and second side portions forming the sides of at least one of the apertures also has a cerclage wire bore extending therethrough.

20 Claims, 4 Drawing Sheets

TROCHANTERIC CERCLAGE PLATE

BACKGROUND OF THE INVENTION

The present invention relates to a bone fixation system, and particularly (though not exclusively) to a system that may be employed in bone implant surgery such as hip replacement operations, or subsequent surgical treatment of the bone structure in the region of an implant. The term "bone fixation" is intended to cover not only the connection of bone to bone but also the connection of components to bone.

More specifically, the invention relates to bone plates that utilize cerclage wire to fix the plate, at least in part to bone. Such devices have been used to reattach trochanteric bone to the femur.

Cerclage is a known fixation technique in which a bone is encircled by a flexible member such as a cable which is drawn tight and clamped. This may serve to hold portions of bone or bone graft together and/or to retain some surgically applied component. For an account of current cable techniques for trochanteric reattachment, femoral allograft fixation and fractures of the proximal femur in revision total hip arthroplasty, the reader is referred to D. M. Dall, *Techniques in Orthop.* 1991; 6(3):7–16. This describes, among other things, use of a bone fastener for the greater trochanter, as disclosed in U.S. Pat. No. 4,269,180. This known bone fastener is a generally H-shaped implant comprising a base structure including a pair of limbs joined by a bridge, the bridge being bounded by a front face, a rear face and edge faces, a plurality of teeth protruding from the base structure, all the teeth lying on the same side of the base structure, and at least one hole in the base structure for receiving a cable, the hole being elongate in form, extending lengthways through the bridge, and being open at each end. The bridge is adapted to be crimped so that cable(s) can be passed through the hole(s), pulled tight, and then locked by crimping. An A-shaped version of this plate is shown in U.S. Pat. No. 6,066,141. Another bone plate system using a crimpable bridge is shown in U.S. Pat. No. 5,665,089, the teachings of U.S. Pat. No. 5,665,089 are incorporated herein by reference.

FIG. 1 of U.S. Pat. No. 5,665,089 is a drawing, taken from the cited paper, shows a femur 10 that has undergone reconstructive surgery including use of a fastener 12 according to U.S. Pat. No. 4,269,180. In this procedure, the greater trochanter 16 was cut (osteotomised) to facilitate installation in the bone cavity of an internal bone graft 14 and the stem of a prosthesis (not shown). Thereafter the greater trochanter 16 was reattached to the femur 10 by means of the fastener 12 and cerclage cables 18. In addition, a fracture 20 of the femur was surgically treated with a further application of cerclage techniques. Thus elongate medial and lateral bone grafts 22 have been applied to the bone, and bound in place by a multiplicity of cerclage cables 25, each of which has been drawn tight and had its ends locked by crimping in an individual crimp sleeve 26.

A typical prior art plate as shown in U.S. Pat. No. 5,665,089 has a unitary body having the form of a pair of side limbs connected by bridges. Thus, there are defined a plurality of apertures or openings preferably each approximately rectangular in plan. Typically, the bone contacting end of the plate is curved to conform to the surface of the bone to which it is to be applied. Pairs of holes or bores pass through the plate in the region of each bridge.

Each aperture is delimited by a wall that generally extends at right angles to the upper surface of the plate.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

SUMMARY OF THE INVENTION

It is one aspect of the invention to provide a bone plate which can accommodate at least two loops of cerclage wire and having an integral bridge capable of clamping the two wire loops in a fixed position.

It is yet another aspect of the invention to provide an implant for the reattachment of a resected greater trochanter that allows for better securement of the bone plate to the femur. These and other aspects of the invention are provided for in a bone fixation system comprising at least one cerclage cable and an elongate bone plate having a bone contacting surface. The bone plate includes first and second spaced side portions and an outer surface opposite the bone contacting surface. The elongate plate has a plurality of apertures or openings therethrough surrounded by the side portions. The apertures extend from the outer surface to the bone contacting surface and are spaced to form bridge portions between adjacent apertures. Each of the bridge portions includes at least two throughbores for receiving cerclage wire. The throughbores in the bridges extend entirely across the plate from the first to the second side portions which bridge portions may be deformed to crimp the cable after it has encircled the bone. At least one of the apertures or openings has a cerclage wire bore extending through the side portions which form the sides of the aperture. Preferably, the bores are axially aligned and extend generally perpendicular to the longitudinal axis of the bone plate. The bores may be placed adjacent the bridge portion so that a first end of a cerclage wire can be inserted into one bore in the bridge portion with a second end wrapped partially around the bone then extending through the aligned bores in the sidewall portions, thus traversing the aperture, with the second end further being wrapped around the bone extending into the other bore in the bridge portion. The bridge portion is then crimped to fix the double-looped cable in place. Preferably, the first cerclage wire end is placed first through the bridge bore furthest from the aperture so that the second wire end is lastly inserted into the bridge bore adjacent the bores in the aperture.

The bone plate may have a plurality of apertures, each adjacent apertures separated by a bridge so that a series of separate cerclage wires can be crimped as described above. When used to attach a trochanter the bone plate may have a first end wherein the first and second side portions are formed as a hooked-shaped portion having a bone contacting surface. Preferably, the hooked-shaped portion is bifurcated, thus forming a first and second hooked-shaped arm portion. The hooked-shaped arm portion is designed to surround the proximal portion of the trochanter. The first and second hooked-shaped arm portions may include two apertures separated by a bridge having a pair of cerclage wire bores that are through. The ends of the hooked-shaped arm portions can be provided with a bone engaging tip that may end in a sharp point. In addition, to the hooked-shaped portions at the first plate end a second pair of hooked-shaped portions may be placed or at a second location on the bone plate. For example, the plate may include a hooked clamping portion extending transversely to the long axis of the plate with one hooked arm extending from each side portion for engaging a curved outer surface of a bone. The transverse curved portion may extend from each side of the hooked portion at the first end of the bone plate and preferably extends laterally in a perpendicular direction to the longitudinal axis of the bone plate. In addition, the bone plate may include a plurality of spikes extending outwardly from the bone contacting surface to engage the bone and thereby help position the plate thereon. The bone plate can have a second end which is adapted to extend along the shaft of a long bone.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
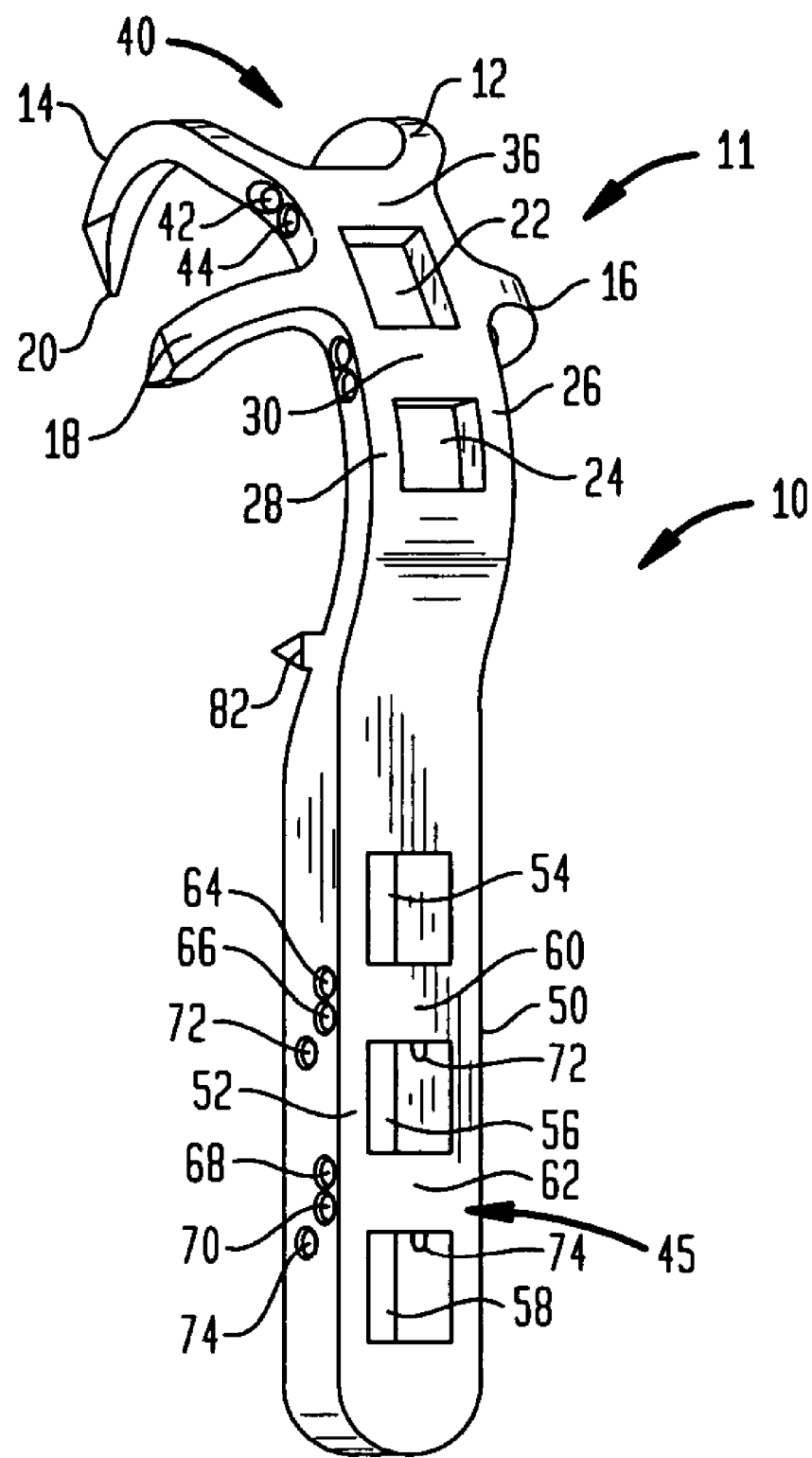
FIG. 1 is a top isometric view of the bone plate of the present invention.
Figure 1A:
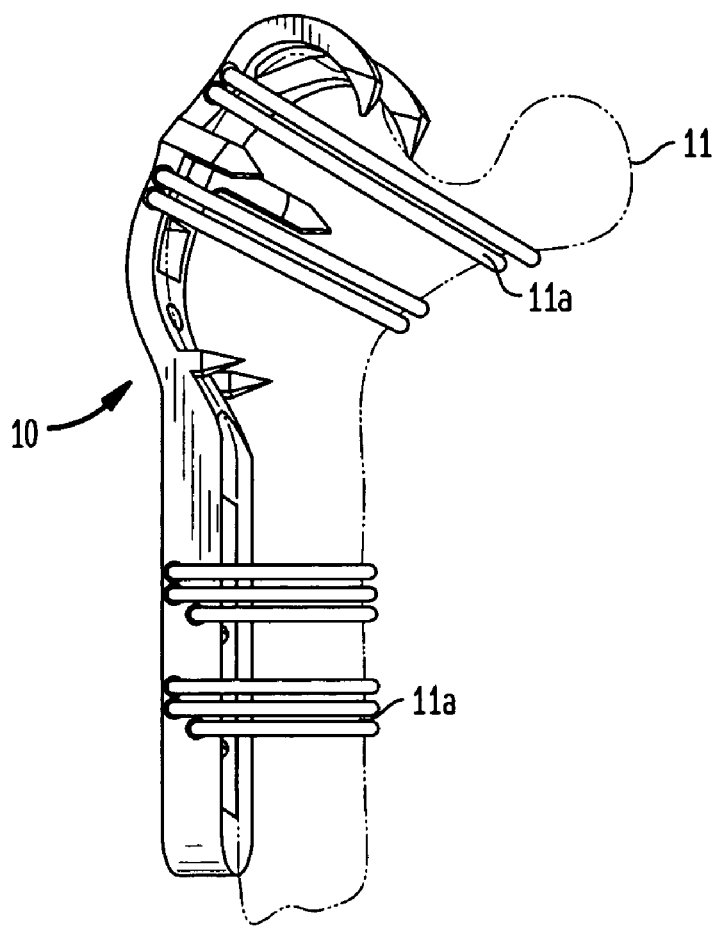
FIG. 1A is a side view of the plate of FIG. 1 on a femur.
Figure 2:
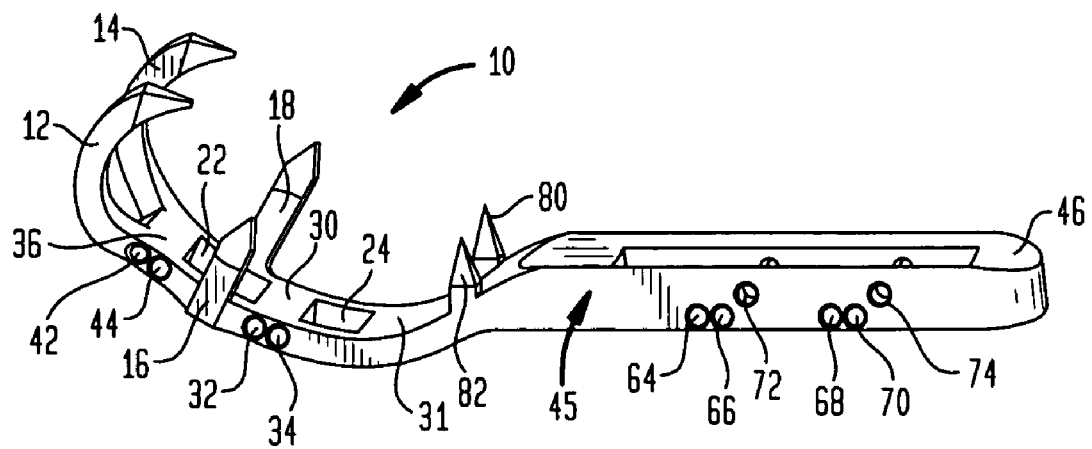
FIG. 2 is a side isometric view of the bone plate of FIG. 1.
Figure 3:
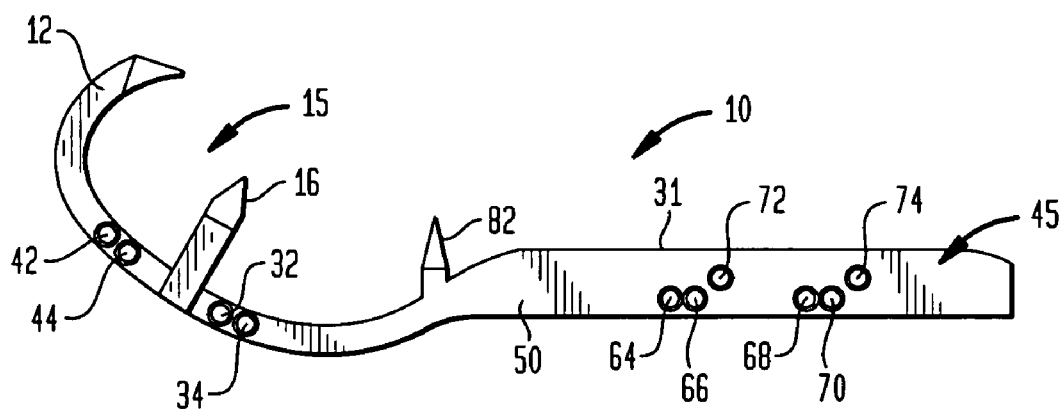
FIG. 3 is an elevation view of the bone plate shown in FIG. 2.
Figure 4:
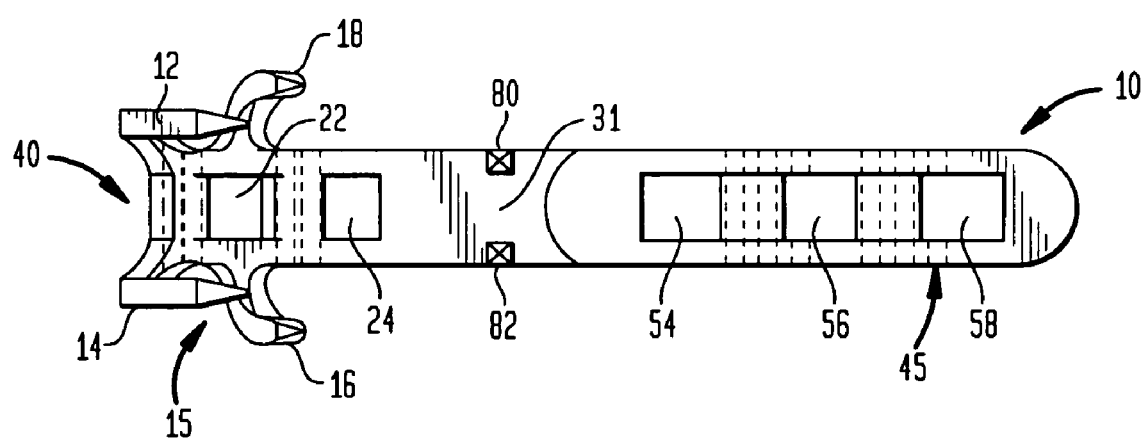
FIG. 4 is a bottom view of the bone plate shown in FIGS. 1–3 with the throughbores shown in phantom.
Figure 5:
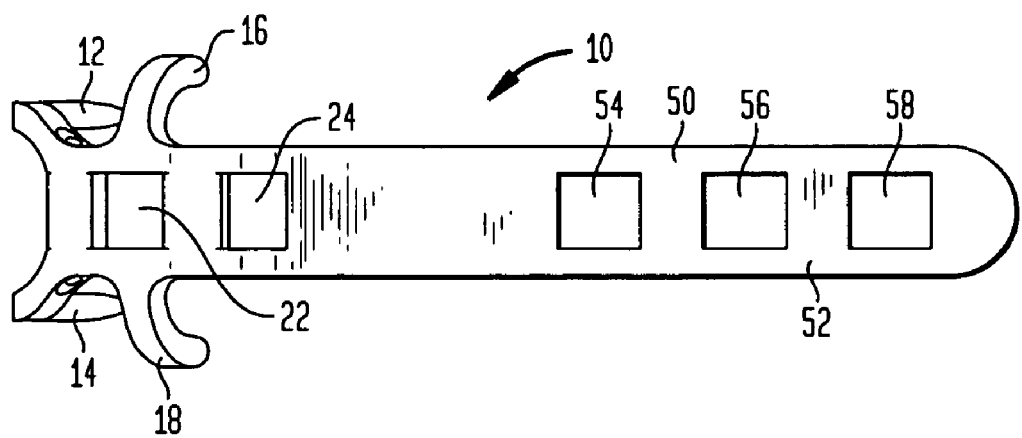
FIG. 5 is a top view of the bone plate of FIGS. 1–4.

Referring to FIGS. 1–5, there is shown a bone plate generally denoted as 10 configured for use in attaching a resected greater trochanter to the femur 11 with cerclage wire 11*a*. A bone plate having the same unique design features may be used in other applications such as to fix long bone fractures. In the preferred embodiment for use with the greater trochanter as shown in FIGS. 1–5, plate 10 includes a first end 11 with a pair of hooked-shaped arm portions 12 and 14 and a pair of laterally extending arms 16 and 18. Arms 12 and 14 have end portions 20 with a tip preferably shaped as a point for engaging bone. The first end of plate 10 also includes a pair of apertures 22 and 24 surrounded on each lateral side by side portions 26 and 28. Apertures 22 and 24 are separated by a bridge portion 30. Bridge portion 30 includes a pair of cerclage wire bores 32 and 34. In the preferred embodiment, arms 12 and 14 are extensions of sidewalls 26 and 28 of the first end of the bone plate 10. As can be seen in the figures, arms 12 and 14 extend in the plate axial direction outwardly from bridge portion 36 and extend in a bifurcated manner with a space 40 therebetween. In the preferred embodiment, bridge 36 also includes a pair of cerclage wire bores 42 and 44.

In the preferred embodiment, plate 10 has a second end 45 adapted to overly the shaft of the femur and in the preferred embodiment may have a concave bone facing surface 46 for engaging the surface of the femur. Second end 45 includes a pair of side portions 50 and 52 formed around a plurality of apertures 54, 56 and 58. Adjacent apertures 54, 56 and 58 are separated by bridge portions 60 and 62 respectively. In the preferred embodiment, bridge portions 60 and 62 include a pair of cerclage wire throughbores 64, 66, 68 and 70 respectively. All of the bridge portions 30, 36, 60 and 62 are deformable in a known manner such as described in U.S. Pat. Nos. 4,269,180 and 5,665,089 to crimp cerclage cable (not shown) in position. While each bridge preferably has two bores for cerclage wire, it would be possible to include three bores in each bridge so long as the crimping operation could collapse the outer two bores. At first end 11, bridges 30 and 36 have two holes and because of the relatively thin cross section of the arms, openings 22 and 24 have no cross-bores.

In addition to bores 64, 66 and 68, 70, the side walls 50 and 52 surrounding apertures 56 and 58 also include throughbores 72 and 74 respectively. Thus, either in or adjacent each bridge 60 and 62, there is located three throughbores for receiving cerclage wire. The three throughbores allow two passes of the wire around the bone, such as the femur, and the locking of the wire forming the two loops within bridges 60 and 62 in a standard manner.

Thus, during implantation of the plate of FIGS. 1–5, arms 12, 14 and 16, 18 are placed over the femur so that the bone contacting surface 31 of the plate 10 engages the trochanteric region of the femur. The function of arms 16 and 18 is to prevent lateral movement of the bone plate on the bone. In addition, in the preferred embodiment, a pair of spikes 80 and 82 may be located extending outwardly from bone contacting surface 31 of the plate to further ensure the fixation of the plate both in the proximal-distal direction and in the lateral direction after the plate is clamped using cerclage wire.

Once arms 12, 14, 16 and 18 are positioned over the proximal femur, one end of a cerclage wire is passed into one of the holes 42, 44 from one side wall, then the other end is wrapped around the femur and placed in the other of the holes 42, 44 from the opposite sidewall. The bridge 36 is then crimped thereby locking the cerclage wire in position around the bone. Similarly, cerclage wire is inserted into holes 32 and 34 and the bridge 30 crimped. At the second plate end 45, however, the aperture side walls have aligned holes 72 and 74 and a cerclage wire is first inserted from one side wall into hole 64 and the other end of the cerclage wire is wrapped around the bone and inserted through hole 72 from the opposite side wall and then again passed around the bone and inserted into the hole 66 from the opposite side wall as the first end of the wire and then once the wire is tightened, bridge 60 may be deformed to thereby crimp the cerclage wire in place. It can be seen that the use of three holes results in two loops of cerclage wire surrounding the bone, such as the femur. Likewise, cerclage wire holes 68, 70 and 74 are utilized to form two loops around the bone and the cerclage wire in bores 68 and 70 is fixed in position by deforming bridge 62. If sufficient material is available, bridges 30 and 36 at the first end 15 of bone plate 10 could also be utilized with three holes with an additional hole extending through the side walls 26 and 28 surrounding apertures 22 and 24. Preferably, hole 74 is centered between the upper and lower surfaces of the plate while holes 68 and 70 are centered within bridges 60, 62 which are not as thick as the plate in the distal area as shown in FIG. 6

Figure 6:
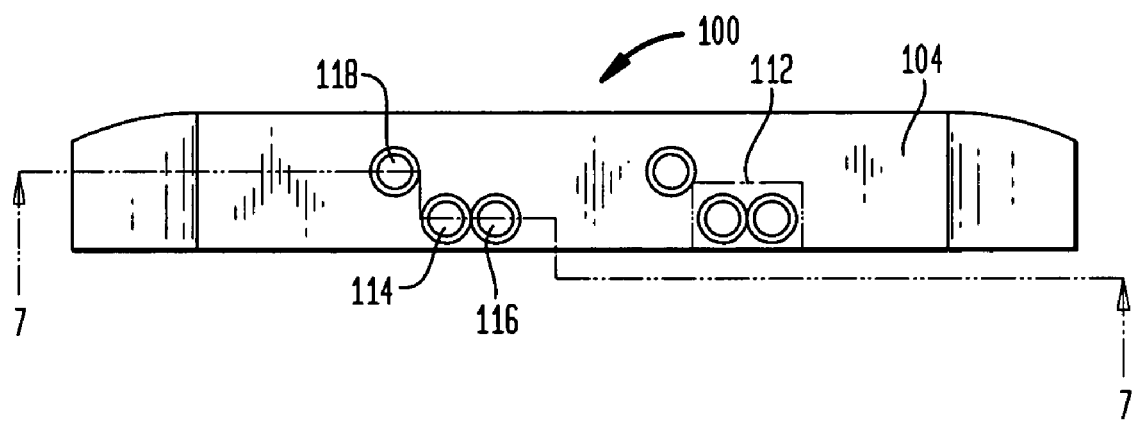
FIG. 6 is a side view of an alternate embodiment of the bone plate of the present invention.
Figure 7:
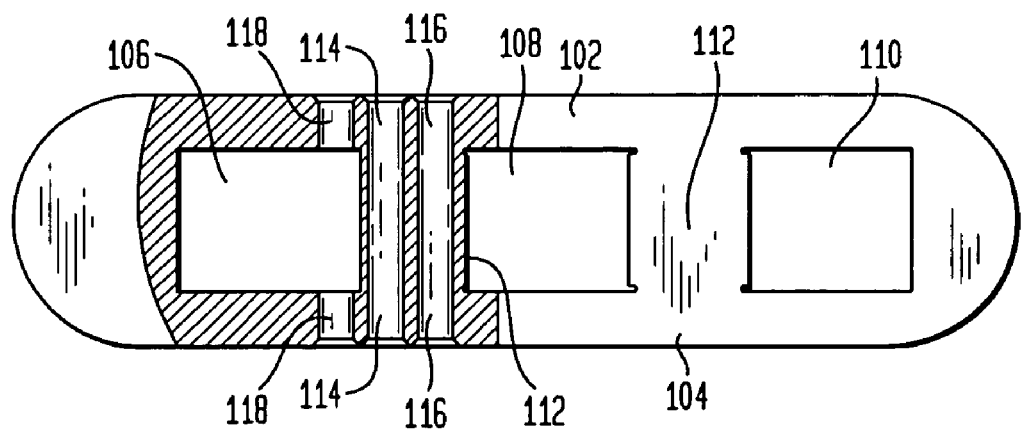
FIG. 7 is a top view of the bone plate of FIG. 6 partially in cross-section.

Referring to FIGS. 6 and 7, there is shown a bone plate for use on any long bone portion where cerclage wire may be used generally denoted as 100. Plate 100 includes a pair of side walls 102 and 104 surrounding a series of apertures 106, 108 and 110. Apertures 106 and 108 are separated by a bridge portion 112 having a pair of throughbores 114 and 116. Obviously, for a longer bone plate 100, additional apertures 106, 108 and 110 could be provided with adjacent apertures being separated by additional bridge portions 112.

In the preferred embodiment, apertures 106 and 108 adjacent bridges 112 are provided with an additional throughbore 118 extending through the aperture side walls 102 and 104. Preferably, the bores 118 in each side wall are aligned.

When attached to a long bone with cerclage wire, plate 100 is attached in a similar manner as is second end 45 of bone plate 10. Thus, one end of a cerclage wire would be inserted into bore 116 with the other end of the cerclage wire being wrapped around a bone and inserted into bore 118 on side wall 102 through aperture 106 out through aperture 118 on side wall 104 again wrapped around the bone and then placed into bore 114 from the side of bone plate 100 having side wall portion 102 and then bridge 112 is crimped to lock the wire in position with respect to bone plate 100. All of the bridges of bone plate 100 would be utilized in the same manner to attach the bone plate to the bone using two loops of cerclage wire.

It should be noted that the bores running through the side walls in the apertures could be placed on both sides of a bridge 112 which would give the surgeon the option of looping the wire on either side of the bridge. However, only one throughbore such as 118 extending through adjacent apertures should be utilized if it is desired to have two loops of cerclage wire around the bone. Of course, additional holes could be supplied in the bridge or in the adjacent apertures if more than two loops are desired.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone fixation system comprising:
at least one cerclage cable;
an elongate bone plate having a bone contacting surface, first and second spaced side portions and an outer surface opposite said bone contacting surface, said elongate plate having a plurality of apertures therethrough surrounded by said side portions, said apertures extending from said outer surface to said bone contacting surface and spaced to form at least one bridge portion between adjacent apertures, each of said bridge portions including at least two through bores extending between said first and second side portions for receiving said cerclage cable, each of said first and second side portions forming the sides of at least one of said apertures having a cerclage wire bore extending therethrough and into at least one of said apertures;
wherein said elongated bone plate further comprises a proximal end and a distal end, said elongated bone plate has a pair of side limbs extending in a proximal distal direction, said side limbs having at least one bridge extending therebetween and at least one cerclage wire extending across each of said limbs and said bridge, a first pair of arms extending from said limbs in a proximal distal direction for abutting the greater trochanter and at least one pair of arms extending from said limbs in a direction transverse to said first pair of arms.

2. The bone fixation system as set forth in claim 1 wherein said bore extending through said side portions surrounding said aperture is positioned adjacent a side edge of one of said bridges.

3. The bone fixation system as set forth in claim 2 wherein each of said through bores in said bridges are positioned within said bridge such that crimping side edges of said bridges substantially closes said pair of through bores to secure said cerclage cable.

4. The bone fixation system as set forth in claim 1 wherein said elongate bone plate has a first end wherein said first and second side portions form a hooked shaped portion having a bone contacting surface.

5. The bone fixation system as set forth in claim 4 wherein said hooked shaped portion is bifurcated having a first and second hooked shaped arm portion.

6. The bone fixation system as set forth in claim 5 wherein the first and second hooked shaped arm portions include at least two apertures separated by a bridge having a pair of cerclage wire bores therein extending between the first and second hook shaped arm portions.

7. The bone fixation system as set forth in claim 6 wherein each hooked shaped arm portion has an end with a bone engaging pointed tip.

8. The bone fixation system as set forth in claim 6 wherein the transversely extending arms are located towards the distal end from the bridge extending between the first and second hook shaped arm portions.

9. The bone fixation system as set forth in claim 4 wherein said first plate end includes a curved portion extending transversely from each side portion of said hooked portion for engaging a curved outer surface of a bone.

10. The bone fixation system as set forth in claim 9 wherein said bone plate includes a pair of spikes extending outwardly of said bone contacting surface of said plate.

11. The bone fixation system as set forth in claim 10 wherein each spike of said pair of spikes is adjacent each sidewall.

12. A bone fixation system comprising:
at least one cerclage cable;
an elongate bone plate having a bone contacting surface, first and second spaced side portions and an outer surface opposite said bone contacting surface, said elongate plate having a plurality of apertures therethrough surrounded by said side portions, said apertures extending from said outer surface to said bone contacting surface and spaced to form at least one bridge portion between adjacent apertures, each of said bridge portions including at least two through bores extending between said first and second side portions for receiving said cerclage cable, each of said first and second side portions forming side walls of at least one of said apertures with each side wall having bores aligned axially;
wherein said elongated bone plate has a proximal end and a distal end, said elongated bone plate has a pair of side limbs extending in a proximal distal direction, said side limbs having at least one bridge extending therebetween and at least one cerclage wire extending across each of said limbs and said bridge, a first pair of arms extending from said limbs in a proximal distal direction for abutting the greater trochanter and at least one pair of arms extending from said limbs in a direction transverse to said first pair of arms.

13. The bone fixation system as set forth in claim 12 wherein said bore extending through said side portions surrounding said aperture is positioned adjacent a side edge of one of said bridges.

14. The bone fixation system as set forth in claim 13 wherein each of said through bores in said bridges are positioned within said bridge such that crimping side edges of said bridges substantially closes said pair of through bores to secure said cerclage cable.

15. The bone fixation system as set forth in claim 12 wherein said elongate bone plate has a first end wherein said first and second side portions form a hooked shaped portion having a bone contacting surface.

16. The bone fixation system as set forth in claim 15 wherein said hooked shaped portion is bifurcated having a first and second hooked shaped arm portion.

17. The bone fixation system as set forth in claim 16 wherein the first and second hooked shaped arm portions include at least two apertures separated by a bridge having a pair of cerclage wire bores therein extending between the first and second hook shaped arm portions.

18. The bone fixation system as set forth in claim 17 wherein each hooked shaped arm portion has an end with a bone engaging pointed tip.

19. The bone fixation system as set forth in claim 15 wherein said first plate end includes a curved portion extending transversely from each side portion of said hooked portion for engaging a curved outer surface of a bone.

20. The bone fixation system as set forth in claim 19 wherein said bone plate includes a pair of spikes extending outwardly of said bone contacting surface of said plate.

* * * * *

UNITED STATES PATENT AND TRADEMARK OFFICE
CERTIFICATE OF CORRECTION

| | | |
|---|---|---|
| PATENT NO. | : 7,229,444 B2 | |
| APPLICATION NO. | : 10/925427 | |
| DATED | : June 12, 2007 | |
| INVENTOR(S) | : Harold S. Boyd | |

It is certified that error appears in the above-identified patent and that said Letters Patent is hereby corrected as shown below:

On the title page item (74), line 2, delete the name "Mentlink" and insert the name --Mentlik--.

On the title page item (57), line 9, in the Abstract, delete the word "including" and insert the word --includes--.

Signed and Sealed this

Tenth Day of June, 2008

JON W. DUDAS
*Director of the United States Patent and Trademark Office*